US010646726B2

(12) United States Patent
Fishman

(10) Patent No.: US 10,646,726 B2
(45) Date of Patent: May 12, 2020

(54) ROBOTIC INTRAOPERATIVE RADIATION THERAPY

(71) Applicant: Sensus Healthcare, Inc., Boca Raton, FL (US)

(72) Inventor: Kalman Fishman, Boca Raton, FL (US)

(73) Assignee: SENSUS HEALTHCARE, INC., Boca Raton, FL (US)

( * ) Notice: Subject to any disclaimer, the term of this patent is extended or adjusted under 35 U.S.C. 154(b) by 341 days.

(21) Appl. No.: 15/649,361

(22) Filed: Jul. 13, 2017

(65) Prior Publication Data

US 2018/0015303 A1    Jan. 18, 2018

Related U.S. Application Data

(60) Provisional application No. 62/361,715, filed on Jul. 13, 2016.

(51) Int. Cl.
*A61N 5/10* (2006.01)
*A61B 90/00* (2016.01)
(Continued)

(52) U.S. Cl.
CPC .......... *A61N 5/1007* (2013.01); *A61B 34/20* (2016.02); *A61B 34/30* (2016.02); *A61B 90/37* (2016.02); *A61B 90/50* (2016.02); *A61N 5/1049* (2013.01); *A61N 5/1083* (2013.01); *A61B 2034/301* (2016.02); *A61B 2090/378* (2016.02); *A61B 2090/3784* (2016.02); *A61N 2005/1008* (2013.01); *A61N 2005/1061* (2013.01)

(58) Field of Classification Search
CPC .. A61N 5/1007; A61N 5/1083; A61N 5/1049; A61N 2005/1008; A61N 2005/1061; A61B 34/20; A61B 90/37; A61B 90/50; A61B 34/30; A61B 2090/378; A61B 2090/3784; A61B 2034/301
See application file for complete search history.

(56) References Cited

U.S. PATENT DOCUMENTS

| 4,401,406 A | 8/1983 | Rovira |
| 5,621,214 A | 4/1997 | Sofield |

(Continued)

FOREIGN PATENT DOCUMENTS

WO     2010030463     3/2010

OTHER PUBLICATIONS

International Search Report and Written Opinion dated Aug. 8, 2018 in PCT/US18/25438.

(Continued)

*Primary Examiner* — Christine S. Kim
(74) *Attorney, Agent, or Firm* — Fox Rothschild LLP

(57) ABSTRACT

Intraoperative radiation therapy involves a treatment head disposed on a distal end of a robotic arm. An X-ray component included as part of the treatment head generates therapeutic radiation in the X-ray wavelength range. At least one patient motion sensor detects a breathing movement of a patient body. A control system dynamically controls a position of the treatment head by causing a position variation in at least one of the movable joints comprising the robotic arm. This movement is managed so that a relative motion as between the treatment head and a tumor bed internal of the patient is minimized.

14 Claims, 6 Drawing Sheets

(51) Int. Cl.
*A61B 90/50* (2016.01)
*A61B 34/20* (2016.01)
*A61B 34/30* (2016.01)

(56) References Cited

U.S. PATENT DOCUMENTS

| | | | |
|---|---|---|---|
| 5,635,709 A | 6/1997 | Sliski et al. | |
| 5,635,721 A | 6/1997 | Bardi et al. | |
| 6,144,875 A * | 11/2000 | Schweikard | A61N 5/1049 |
| | | | 378/69 |
| 6,207,952 B1 | 3/2001 | Kan et al. | |
| 6,826,254 B2 | 11/2004 | Mihara et al. | |
| 6,977,987 B2 | 12/2005 | Yamashita et al. | |
| 7,005,623 B2 | 2/2006 | Neuberger et al. | |
| 7,140,771 B2 | 11/2006 | Leek | |
| 7,188,999 B2 | 3/2007 | Mihara et al. | |
| 7,193,220 B1 | 3/2007 | Navarro | |
| 7,200,203 B2 | 4/2007 | Cocks et al. | |
| 7,239,684 B2 | 7/2007 | Hara et al. | |
| 7,263,170 B2 | 8/2007 | Pellegrino | |
| 7,266,176 B2 | 9/2007 | Allison et al. | |
| 7,283,610 B2 | 10/2007 | Low et al. | |
| 7,356,120 B2 | 4/2008 | Main et al. | |
| 7,420,160 B2 | 9/2008 | Delaperriere et al. | |
| 7,505,559 B2 | 3/2009 | Kuduvalli | |
| 7,590,219 B2 | 9/2009 | Maurer, Jr. et al. | |
| 7,605,365 B2 | 10/2009 | Chen et al. | |
| 7,619,374 B2 | 11/2009 | Aoi et al. | |
| 7,656,998 B2 | 2/2010 | Main et al. | |
| 7,686,755 B2 | 3/2010 | Smith et al. | |
| 7,693,257 B2 | 4/2010 | Allison | |
| 7,713,205 B2 * | 5/2010 | Fu | A61B 8/08 |
| | | | 600/437 |
| 7,894,649 B2 | 2/2011 | Fu et al. | |
| 7,902,515 B2 | 3/2011 | Navarro | |
| 8,050,384 B2 | 11/2011 | Carol et al. | |
| 8,126,114 B2 | 2/2012 | Naylor et al. | |
| 8,180,020 B2 | 5/2012 | Kilby et al. | |
| 8,183,522 B2 | 5/2012 | Celi de la Torre et al. | |
| 8,295,435 B2 * | 10/2012 | Wang | A61N 5/10 |
| | | | 378/65 |
| 8,303,476 B2 | 11/2012 | Francescatti et al. | |
| 8,321,179 B2 | 11/2012 | Simon et al. | |
| 8,520,801 B2 | 8/2013 | Henning | |
| 8,559,596 B2 | 10/2013 | Thomson et al. | |
| 8,559,598 B2 | 10/2013 | Kindlein et al. | |
| 8,602,647 B2 | 12/2013 | Navarro | |
| 8,655,429 B2 | 2/2014 | Kuduvalli et al. | |
| 8,660,235 B2 | 2/2014 | Koehler | |
| 8,792,613 B2 | 7/2014 | Gardner et al. | |
| 8,804,901 B2 | 8/2014 | Maurer, Jr. et al. | |
| 8,917,813 B2 | 12/2014 | Maurer, Jr. | |
| 8,929,511 B2 | 1/2015 | van der Veen et al. | |
| 8,934,605 B2 | 1/2015 | Maurer, Jr. et al. | |
| 8,989,846 B2 | 3/2015 | Kuduvalli et al. | |
| 8,995,616 B2 | 3/2015 | van der Veen et al. | |
| 9,036,787 B2 | 5/2015 | de Jager | |
| 9,108,048 B2 | 8/2015 | Maurer, Jr. et al. | |
| 9,168,391 B2 | 10/2015 | Henning et al. | |
| 9,289,268 B2 | 3/2016 | Ramraj et al. | |
| 9,333,031 B2 | 5/2016 | Salahieh et al. | |
| 9,415,239 B2 | 8/2016 | Lubock et al. | |
| 9,561,009 B2 | 2/2017 | Woudstra et al. | |
| 9,616,251 B2 | 4/2017 | Filiberti et al. | |
| 9,724,066 B2 | 8/2017 | Van Der Veen et al. | |
| 9,743,912 B2 | 8/2017 | Fichtinger et al. | |
| 2004/0218721 A1 | 11/2004 | Chornenky et al. | |
| 2004/0227056 A1 | 11/2004 | Neuberger et al. | |
| 2005/0276377 A1 | 12/2005 | Carol | |
| 2006/0085053 A1 | 4/2006 | Anderson et al. | |
| 2007/0076851 A1 | 4/2007 | Pellegrino | |
| 2008/0009659 A1 | 1/2008 | Smith et al. | |
| 2008/0198970 A1 | 8/2008 | Kirshner et al. | |
| 2009/0161826 A1 | 6/2009 | Gertner et al. | |
| 2010/0237259 A1 | 9/2010 | Wang | |
| 2010/0274151 A1 | 10/2010 | Chi et al. | |
| 2011/0105822 A1 | 5/2011 | Roeder | |
| 2012/0016175 A1 | 1/2012 | Roberts et al. | |
| 2013/0025055 A1 | 1/2013 | Saracen et al. | |
| 2013/0116555 A1 * | 5/2013 | Kuzelka | A61B 6/03 |
| | | | 600/427 |
| 2013/0345718 A1 | 12/2013 | Crawford et al. | |
| 2014/0086388 A1 | 3/2014 | Yamada et al. | |
| 2014/0121501 A1 | 5/2014 | Fichtinger et al. | |
| 2014/0171919 A1 * | 6/2014 | Blacker | A61M 39/10 |
| | | | 604/528 |
| 2014/0185778 A1 | 7/2014 | Lee et al. | |
| 2014/0205067 A1 | 7/2014 | Carol et al. | |
| 2014/0348288 A1 | 11/2014 | Boyd et al. | |
| 2015/0366546 A1 * | 12/2015 | Kamen | A61B 5/067 |
| | | | 600/461 |
| 2016/0106387 A1 | 4/2016 | Kahn et al. | |
| 2016/0184032 A1 | 6/2016 | Romo et al. | |

OTHER PUBLICATIONS

International Search Report and Written Opinion dated Sep. 21, 2017 for PCT/US2017/041986.

International Search Report mailed in PCT/IB2018/055352 dated Nov. 26, 2018.

International Search Report and Written Opinion dated Oct. 29, 2018 in PCT/US18/46663.

Extended European Search Report dated Jan. 21, 2020 in EP 17828486.5 filed Jan. 23, 2019.

International Search Report mailed in PCT/US19/57191 dated Feb. 19, 2020.

* cited by examiner

ROBOTIC INTRAOPERATIVE RADIATION THERAPY

CROSS-REFERENCE TO RELATED APPLICATIONS

This application claims priority to U.S. patent application Ser. No. 62/361,715, filed Jul. 13, 2016. The contents of the above application is incorporated by reference its entirety

BACKGROUND

Statement of the Technical Field

The inventive arrangements relate to radiation therapy, and more particularly to robotic systems and methods for intraoperative radiation therapy.

Description of the Related Art

Cancer surgery can involve removal of a cancerous tumor and some normal tissue surrounding the tumor. For example, Breast Conserving Surgery (BCS) is a type of cancer surgery in which a cancerous lump and part of the surrounding breast tissue (as opposed to the entire breast) is removed during surgery. The surgery is usually followed by a moderate-dose radiation therapy which is intended to eradicate any traces of cancerous tissue from a tumor bed (vascular and stromal tissue that surrounds a cancerous tumor). Radiotherapy techniques can involve an externally delivered radiation dose using a technique known as external beam radiotherapy (EBRT). But conventional EBRT can increase the risk of missing an intended target volume. To address this problem, intraoperative radiotherapy (IORT) is sometimes used. IORT involves the application of therapeutic levels of radiation to a tumor bed while the area is exposed and accessible during excision surgery. The benefit of IORT is that it allows a high dose of radiation to be delivered precisely to the targeted area with minimal exposure to surrounding tissues. IORT also avoids the usual delays which are associated with the time between when the surgical removal of the cancerous tissue and the EBRT.

When IORT is appropriate a surgeon will remove a cancerous tumor after which a radiation oncologist will position a radiation applicator in the area where the tumor was previously located. Conventional IORT methods and systems can involve use of electron beams and/or low energy X-Rays. Electron beams used for this purpose can be produced by a linear accelerator as is generally used for radiotherapy with a EBRT. In such scenarios, the patient undergoing surgery is transported from the operating room to a shielded radiotherapy facility, and then returned to the operating room upon completion of the radiotherapy treatment. More recently, dedicated accelerators for use in the operating room have been developed.

SUMMARY OF THE INVENTION

This disclosure concerns a robotic system for intraoperative radiation therapy (IORT). The system includes a robotic arm comprised of a plurality of movable joints. The robotic arm is secured a first end to a base. A treatment head is disposed on a second end of the robotic arm distal from the base. The treatment head comprising at least one X-ray component configured to facilitate generation of therapeutic radiation in the X-ray wavelength range. At least one patient motion sensor is provided for detecting a movement of a patient body associated with breathing (i.e., inspiration and expiration of air into and out of the thoracic cavity). A control system is responsive to patient motion data from the at least one patient motion sensor. The control system is configured to facilitate dynamic position control of the treatment head. It accomplishes this result by selectively varying a position of at least one of the movable joints comprising the robotic arm. Such dynamic position control facilitated by the control system is configured to minimize a relative motion as between the treatment head and a tumor bed internal of the patient while using the treatment head to perform a radiation treatment.

According to one aspect, the control system is configured to selectively control the motion of the treatment head in three orthogonal directions. In some scenarios, these operations can involve selectively controlling the position of the treatment head to minimize variations in distance as between an X-ray source of the therapeutic radiation within the treatment head and internal surfaces of the tumor bed during patient breathing activity. According to another aspect, the control system is configured to selectively control a rotation of the treatment head to minimize angular variations of the source of the therapeutic radiation relative to locations comprising the surfaces of the tumor bed under conditions of patient body movement associated with breathing.

In some scenarios, the patient motion sensor is comprised of a force sensor. The force sensor can be configured to sense a force exerted upon the robotic arm as a result of the patient movement (e.g., patient movement associated with breathing). According to one aspect, the force sensor is comprised of at least one joint sensor which is configured to sense a force exerted on at least one of the plurality of movable joints comprising the robotic arm. Other patient motion sensors can also be used. For example, in some scenarios the patient motion sensor can be an optical sensor configured to detect a position of at least one fiducial marker (e.g. a fiducial marker placed on the body of the patient). It is anticipated that more than one type of sensing can be used to facilitate detection and movement of a patient's body as described herein.

The robotic arm described herein can support a plurality of utility channels to facilitate IORT functions and operations. Such utility channels can include one or more of fluid utility channels, electrical utility channels, and data utility channels. According to a further aspect, an inflatable balloon member is disposed to enclose at least a distal end of the treatment head from which the therapeutic radiation originates. In such scenarios, the fluid utility channels are advantageously configured to communicate a fluid to and from the interior of the balloon member for inflating and deflating the balloon. At least one imaging device can be supported by the robotic arm or the treatment head to facilitate optical guidance of the treatment head within the cavity left by a cancerous tumor after excision thereof. In such scenarios, the data carried by the data utility channel can comprises video or image data. Likewise, an ultrasound probe can be supported on the treatment head. The ultrasound probe or transducer can facilitate ultrasound imaging of a tumor bed within the patient remaining after excision of a cancerous tumor. If such an ultrasound transducer is provided, the data carried by the data utility channel will comprise ultrasound imaging data.

The disclosure also concerns a method for intraoperative radiation therapy. The method involves securing a treatment head on a mounting end of the robotic arm distal from a robotic arm base. At least one X-ray component is included as part of the treatment head; the X-ray component being configured to facilitate generation of therapeutic radiation in the X-ray wavelength range. The method involves detecting with at least one patient motion sensor a movement of a patient body associated with breathing. A control system is provided that is responsive to patient motion data. The control system dynamically controls a position of the treatment head by causing a position variation in at least one of the movable joints comprising the robotic arm. This control of the movable joints is managed so that a relative motion as between the treatment head and a tumor bed internal of the patient is minimized. The dynamic motion control can be performed while using the treatment head to perform IORT.

BRIEF DESCRIPTION OF THE DRAWINGS

The disclosure herein will be with reference to the following drawing figures, in which like numerals represent like items throughout the figures, and in which.

DETAILED DESCRIPTION

Figure 1:
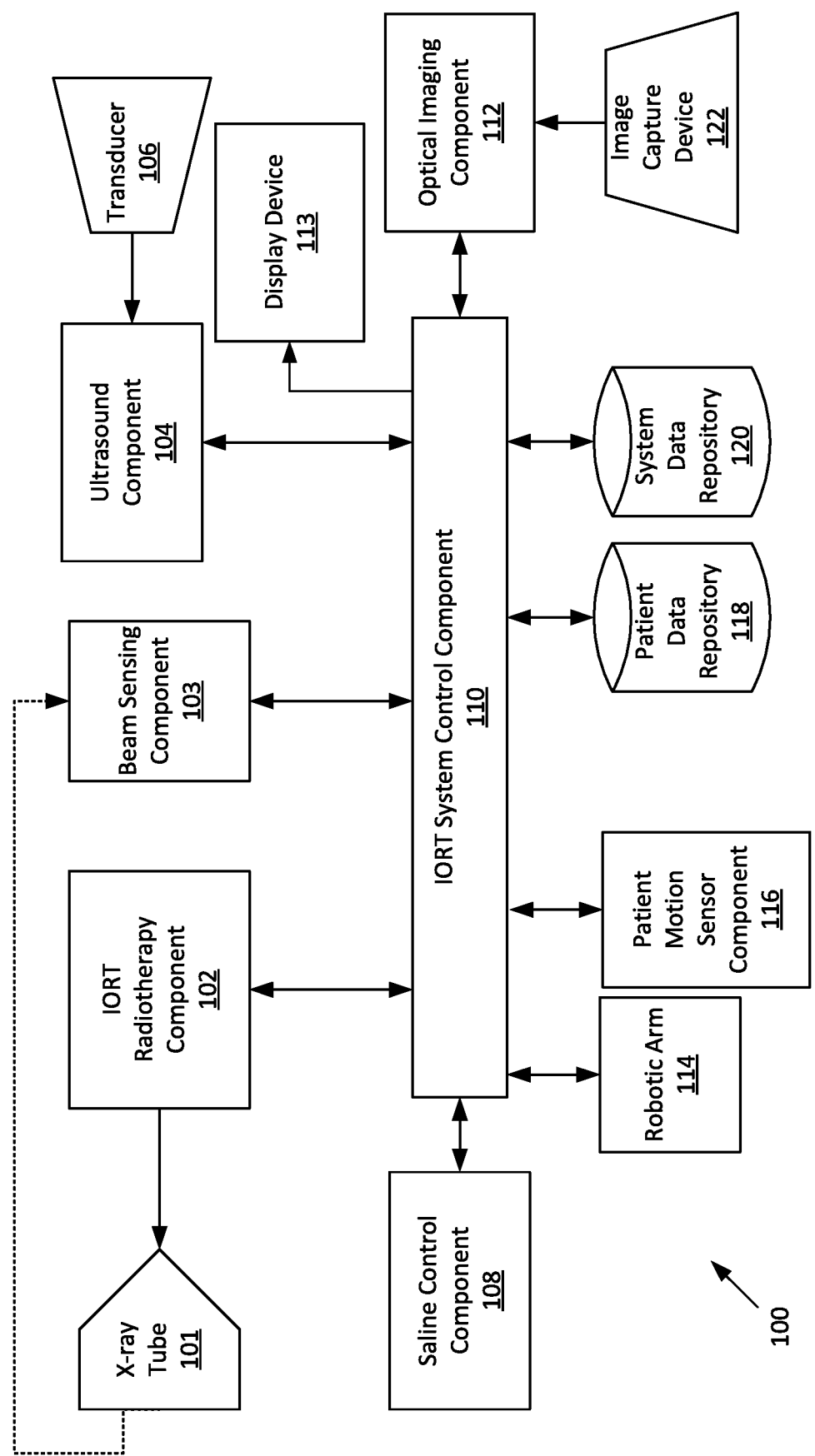
FIG. 1 is a block diagram that is useful for understanding a robotic IORT system.

It will be readily understood that the components of the systems and methods described herein and illustrated in the appended figures could be arranged and designed in a wide variety of different configurations. Thus, the following more detailed description, as represented in the figures, is not intended to limit the scope of the present disclosure, but is merely representative of certain exemplary scenarios which are useful for understanding the disclosure. While the various aspects are presented in drawings, the drawings are not necessarily drawn to scale unless specifically indicated.

One type of low energy X-Ray IORT applicator involves a catheter-like device with a balloon tip. After a tumor has been excised, the catheter is inserted into the cavity where the tumor was previously located, a miniature radiation therapy source is then inserted within the balloon into the cavity to deliver radiation to the tumor bed internally and the balloon is inflated with saline such that the inflated balloon fits snugly within the cavity. The balloon and saline solution are used to help ensure that a homogeneous radiation dose is applied to all portions of the tumor bed. The saline is used to inflate the balloon and reduces radiation attenuation as normally occurs when x-rays travel through air. The saline solution is also constantly circulated within the balloon in order to provide a redundant coolant medium for the X-Ray miniature source during therapy. After a period of time (e.g., 15 minutes) the radiation source and balloon are removed from the cavity and the surgeon closes the incision.

A key aspect to this conventional IORT technique is the miniaturized X-ray source which is sufficiently small so that it can be inserted within a catheter as described. Due to the exceedingly small size and mass of these devices, they can be disposed at the end of the flexible catheter and supported within the saline balloon. This is an important consideration because ordinary respiratory function of a patient receiving IORT can be expected to cause the physical movement of the chest cavity. Since the saline balloon is secured within the tumor bed, the balloon and the X-ray source disposed therein will move with the patient. This prevents movement of the X-ray source relative to the treatment surfaces of the tumor bed and helps ensure that a homogeneous radiation dose is precisely applied to all portions of the tumor bed.

From the foregoing it will be appreciated that miniature X-ray sources can be effective for IORT. Still, the very small X-ray sources used for this purpose have been found to suffer from certain drawbacks. One problem is that the miniature X-ray sources are very expensive. A second problem is that they have a very limited useful operating life. This limited useful operating life typically means that the X-ray source must be replaced after being used to perform IORT on only one or two patients. These two problems greatly increase the cost of IORT for BCS and other types of cancer treatment surgery.

The expense and short operating life associated with miniature X-ray sources can easily be overcome by larger more conventional X-ray sources. But these sources present a different problem when performing IORT. It is important when performing IORT to maintain all of the tissue of the tumor bed at a predefined distance from the radiation source. This ensures homogeneous radiation exposure to the entire tumor bed. A larger more conventional X-ray source must normally be supported on an articulating arm. The articulating arm holds the X-ray source in a fixed position. In contrast, the respiratory function of a patient means that the tissue in and around the chest cavity will be in constant motion. So relative motion between the source and the cavity walls forming the tumor bed make it nearly impossible to ensure that a homogeneous radiation dose is applied to all of the tissue comprising the tumor bed.

The solution to this problem is robotic IORT in which the X-ray source is disposed on a robotic arm. The movement of the robotic arm is synchronized with the respiratory action of the patient so that the X-ray source always has the same relative position to the tissue comprising the tumor bed. The robotic arm supports the X-ray source and provides all necessary utility channels to support IORT functions and operations. For example, the robotic arm can provide primary electric power for operating the X-ray source. The robotic arm can also include one or more liquid conduits to facilitate delivery of saline to an inflatable balloon and for draining saline from the balloon. The robotic arm can also support utility functions to aid a radiation oncologist in positioning the X-ray source. For example, the robotic arm can support a fiber optic for a video camera to facilitate optical guidance of the X-ray source within the cavity left by the cancerous tumor after excision. Alternatively, (or in addition thereto) the robotic arm can support an ultrasound probe to facilitate ultrasound imaging of the tumor bed before, during and after radiation therapy is performed.

With the foregoing arrangement, a more conventional or larger size X-ray source can be used for IORT in place of a miniaturized X-ray source. The conventional X-ray source can provide all of the benefit of a miniature X-ray source but without the added cost associated with the miniature X-ray source. The functional result for the patient is the same as with the miniature X-ray source disposed in a flexible catheter, but the durability and lower cost of the larger conventional X-ray source will greatly reduce the overall cost of IORT treatment.

The various aspects of the present disclosure will be described with respect to the attached drawings of an exemplary system that can deliver both therapeutic IORT functionalities through a single platform to better serve and benefit the practitioner and patient. The exemplary system can include multiple imaging devices and a radiotherapy device used cooperatively to perform IORT in accordance with the present disclosure. Thus, the system can be an image-guided robotic IORT radiotherapy treatment system.

Referring now to FIG. 1 there is shown a high level block diagram representation of a robotic IORT system 100 which is useful for understanding the invention. The exemplary system 100 can include a radiotherapy component 102 with X-ray tube 101, an optional ultrasound component 104 with a transducer 106, an optical imaging (OI) component 112 with an associated image capture device (ICD) 122. The system also includes a robotic arm 114, patient motion sensor 116, and a saline control component 108. The system control component 110 guides the robotic arm 114 during IORT operations based on images and data obtained from one or more of a patient motion sensor component 116, the ultrasound component 104, transducer 106, OI component 112, and ICD 122.

The saline control component can comprise a pump and one or more selectively controlled valves, all under the control of software and hardware elements associated with the system control component. The pump can be connected to a reservoir or source of saline solution. As such, the saline control component can control a flow of saline to and from a balloon (not shown) disposed on the end of a robotic arm 114. When IORT operations are to be performed, the balloon is inserted into a cavity from which a cancerous tumor has been removed and is inflated with saline. Once inflated, the X-ray tube 101 and radiotherapy component 102 are used to apply radiation to the walls of the cavity formed by the tumor bed. During the application of radiation, the saline control component can monitor and maintain fluid circulation and pressure within the balloon. After IORT treatment has been completed, the saline control component 108 releases the saline to deflate the balloon and the balloon is withdrawn from the cavity.

The robotic arm 114 is advantageously selected to be a robotic system that provides freedom of movement about multiple orthogonal axes (e.g. up to seven axes) and includes lightweight force and torque sensors (not shown) to ensure safe operation with humans without the need for a safety fence. Exemplary robots of this kind are commercially available from various sources. For example, KUKA Roboter GmbH of Augsburg Germany (KUKA) manufactures a line of direct human-robot collaboration (HRC) capable lightweight robots which are suitable for direct human-robot interaction. These robots include the LBR iiwa model produced by KUKA. Robots of this kind are well suited for the delicate operations described herein because they include joint torque sensors which can detect contact with objects, and can respond by immediately reducing a level of force and speed associated with robot movements.

The patient motion sensing component 116 can include optical sensors, ultrasound sensors, pressure sensors, laser sensors or any other type of sensor which is useful for monitoring movement of a patient undergoing IORT treatment. For example, such movement may comprise respiratory movement and/or digestive system movement which occurs during IORT. The patient motion sensor component can be separate from the robotic arm 114 and/or may be integrated into the robotic arm to facilitate such sensing. In some scenarios, data from ultrasound component 104, transducer 106, optical imaging component 112, and image capture device 122 can be used for patient motion sensing as described herein. The information from these sensors can be used instead of or in conjunction with sensing data acquired from patient motion sensor component 116.

The system control component 110 receives the patient motion sensor data and uses it to control the robotic arm 114. More particularly, during IORT operations as described herein, a motion of the robotic arm is controlled in accordance with the patient motion sensing data to ensure that the X-ray tube 101 moves in sync with the tissue natural movement due to respiratory or other body functions, which will precisely align the X-Ray source relative to the tumor bed which is receiving radiation therapy. The precise control over the motion and position of the X-ray tube can ensure that all areas of the tumor bed receive a homogenous exposure to the applied radiation. In order to accomplish this result, the robotic arm can move along multiple motion axes (e.g., up to seven motion axes) to maintain its relative position within the cavity from which the cancerous tumor was removed.

The radiotherapy component 102 is utilized to treat a tumor bed in accordance with IORT treatment methods which are now known or known in the future. The X-ray tube 101 is advantageously selected to be an isotropic source for x-ray photon particles to perform IORT of a tumor bed. Further, the X-ray tube is advantageously selected and purposely designed so that it has a relatively small size such that it fits within a cavity from which a cancerous tumor has been removed, yet it is robust and large enough to withstand numerous treatment sessions without burning out, or failing. This approach and design will provide a cost-effective solution for a reusable IORT X-Ray source, which is small enough to fit in most or all post-surgical tumor bed cavities, yet not too physically small, which translates to very short life spans and higher costs of utilization.

The radiotherapy component 102, which can be a superficial radiotherapy component, and X-ray tube 101, can together include control circuitry, one or more cooling elements for the x-ray tube, power supplies, one or more high voltage generator, one or more interchangeable applicators, and one or more hardware timers that work in concert with a software timer for redundancy and other purposes. It is contemplated that the X-ray tube utilized herein will be selected so that is optimized for IORT interaction with tumor bed tissue, and has minimal effects at deeper tissue depths. For example, a conventional superficial radiation therapy (SRT) type of X-ray unit can be used for this purpose. As will be appreciated, an SRT type of X-ray unit produces low energy X-rays that is suitable for this purpose.

In some scenarios, a solid-state X-ray beam sensing component 103 can monitor the beam output of the radiotherapy component 102 and x-ray tube 101, along with overall system stability and yield. The solid-state X-ray beam sensing component 103 is mounted to the X-Ray tube 100 and is moved in front of the tube when the system 150 needs to be tested for quality control, or overall system 150 diagnosis purposes. Otherwise, it is retracted back in its home position, away from the X-ray tube 101 and the X-ray beam in order not to interfere during a IORT operations as described herein.

The present disclosure contemplates that in addition to or as an alternative to using a X-ray based radiotherapy in system 100, any other types of radiotherapy can be used in system 100. Thus, the components for radiotherapy can be selected to support photon-based radiotherapy (e.g., x-rays and gamma rays), particle-based radiotherapy (e.g., electrons, protons, neutrons, carbon ions, alpha particles, and beta particles), or any combinations thereof which may be determined to be suitable for IORT now or in the future.

The ultrasound component 104 can include control circuitry, system drivers, operation control software, and a transducer 104, which can be high frequency ultrasonic transducer, for tissue imaging of the tumor bed. The ultrasound component 104 communicates with the software of the system control component 110 via a bus and system drivers. The ultrasound component 104 and transducer 106 are provided in exemplary system 100 to provide structural or anatomical data associated with the tumor bed without exposing a subject to ionizing radiation. However, the present disclosure contemplates that ultrasound component 104 and transducer 106 can be replaced or supplemented in system 100 with components for supporting any other types of imaging techniques that also do not utilize ionizing radiation. For example, optical coherence tomography or laser range scanning (LIDAR), to name a few.

The ultrasound component 104 can be any ultrasound device capable of operating within an acceptable bandwidth. For example, the ultrasound component and transducer 106 can operate in a bandwidth of approximately 2 MHz to approximately 70 MHz, and may be implemented with an electro-mechanical, or a solid state transducer. The system 100 can provide the ultrasound component 104 at least partially integrated inside a system 100 housing coupled to a data bus, with a transducer head 106 outside of the housing as discussed in relation to FIGS. 2 and 3. The ultrasound component 104 and other components of the system 100, can be in communication with a data bus to facilitate communication of image data to system control component 110 and/or display device 113. A suitable interface standard can be used for this purpose such as peripheral component interconnect (PCI/PCIe), universal serial bus (USB/USBII/USBIII/USB-C), Ethernet, or Firewire. However, the present disclosure contemplates that any other interface and/or communications standards can be used.

The optical imaging component 112 can include control circuitry, system drivers, operation control software, and one or more image capture devices 122, for imaging a tumor bed. According to one aspect, the optical imaging component is a spectroscopic imaging device. For example, the optical imaging component can comprise a multispectral imaging device that captures image data at a plurality of optical frequencies. Such multispectral imaging component can be configured to utilize optical energy from the visible portion of the light spectrum for imaging purposes, but can also utilize optical energy from frequencies beyond the visible light range (e.g. infrared and near ultraviolet). Alternatively, the optical imaging component can comprise a hyperspectral imaging device wherein optical information is captured from across the electromagnetic spectrum at each pixel in the captured image. As a further alternative, the spectroscopic imaging device can be configured for Raman spectroscopy which captures changes in the frequency of photons in monochromatic light which result from interaction with tissue within the tumor bed. As a further alternative, the spectroscopic imaging device can be configured for photoacoustic imaging, which utilizes non-ionizing laser pulses or an alternative light source to image the residual cavity tissue.

The optical imaging component 112 communicates with the software of the system control component 110 via a bus and system drivers. The present disclosure contemplates that optical imaging component 112 and the image capture device 122 can be replaced or supplemented in system 100 with components for supporting any other types of imaging techniques for extracting molecular or functional information from tumor bed tissues. For example, biomarkers can be used to enhance the usefulness of the optical imaging methods described herein. As is known, a biomarker can involve a substance which is introduced to a tissue to facilitate the identification of a disease condition such as cancer. According to one aspect, a biomarker can include any substance introduced to a tumor bed tissue which can be used to induce visually or optically detectable changes that can facilitate identification of cancerous cells. Any biomarker now known or known in the future can be used in conjunction with the optical imaging component 112 and the one or more image capture devices 122 provided that it can help facilitate identification of functional data pertaining to tumor bed tissue under observation.

Figure 2:
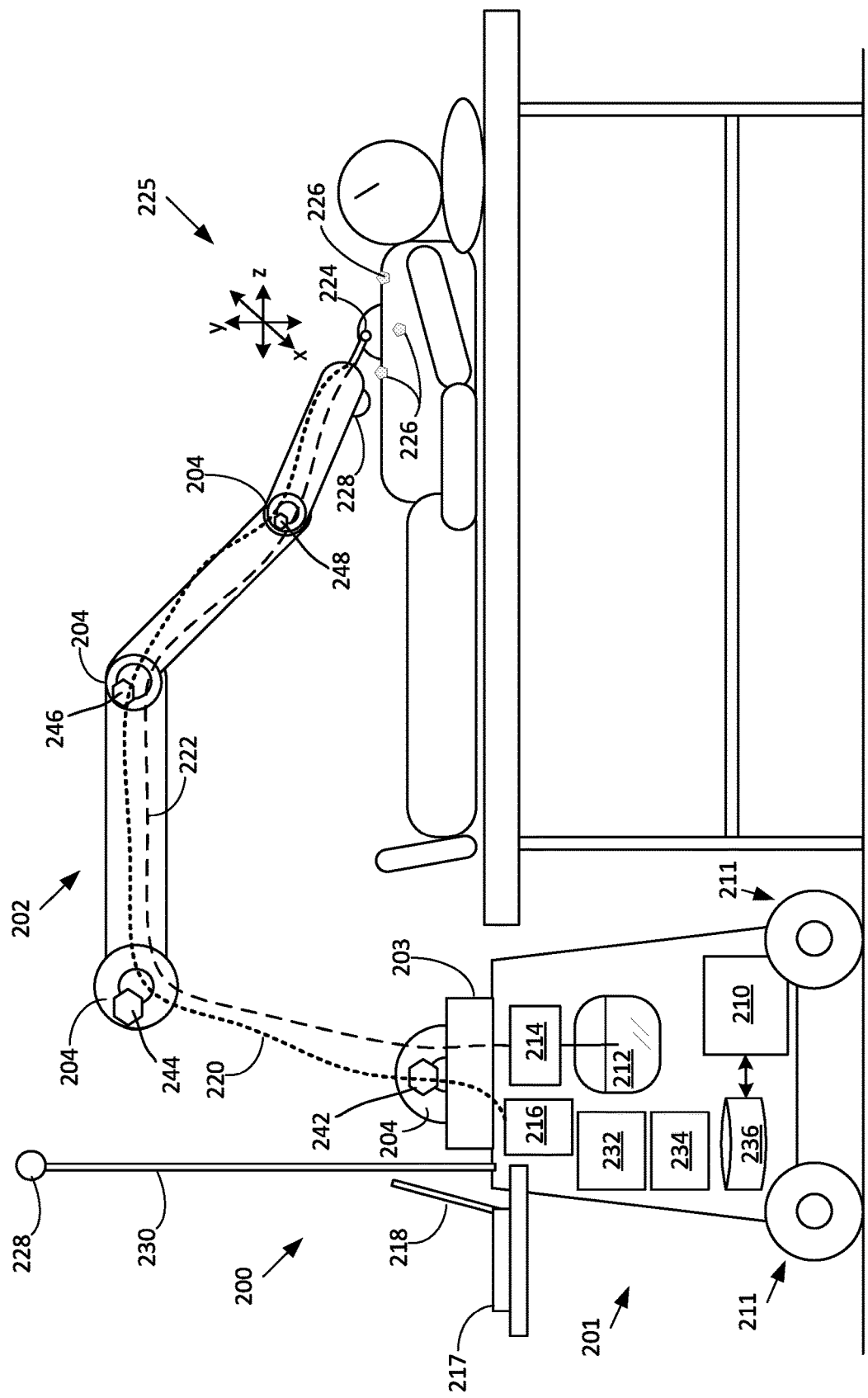
FIG. 2 is a diagram that is useful for understanding an implementation of a robotic IORT using a robotic arm and a treatment head.
Figure 3:
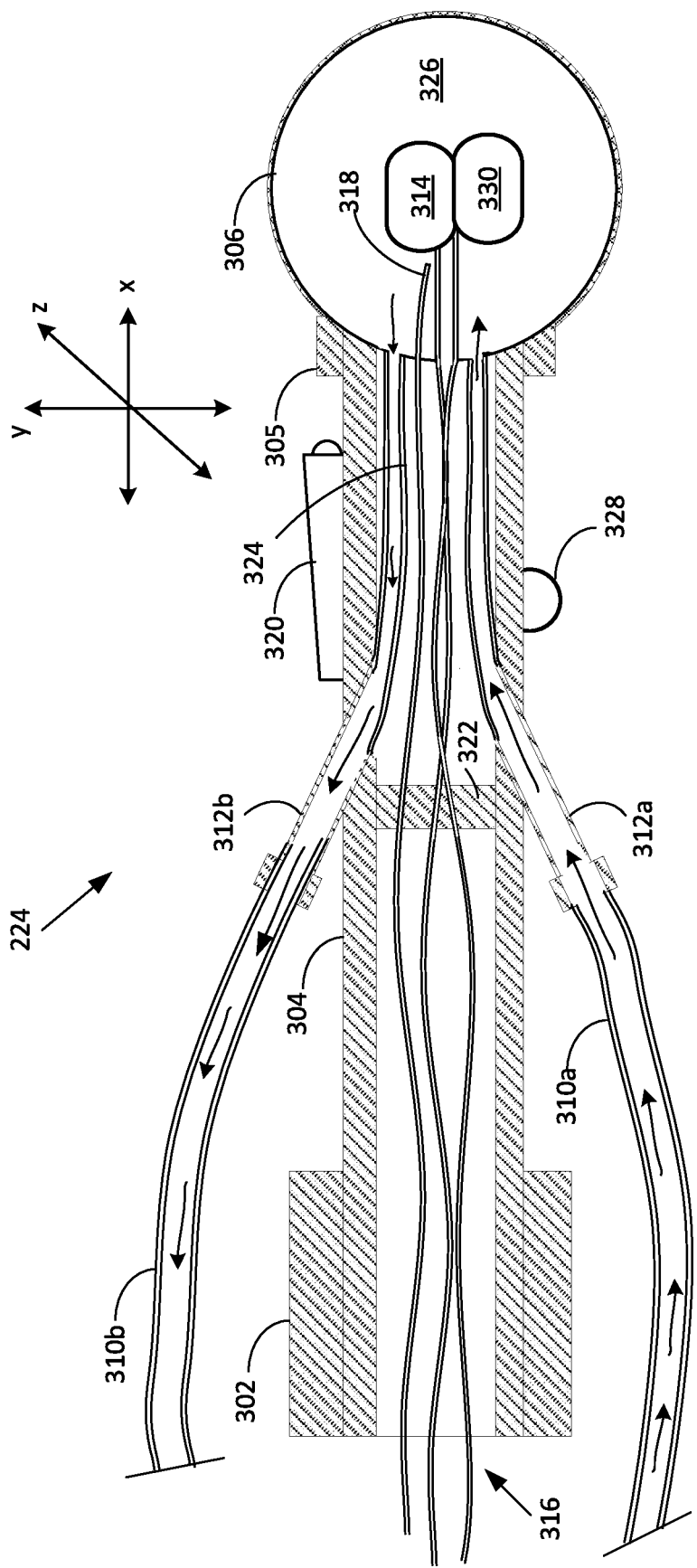
FIG. 3 is a drawing showing a more detailed view of a treatment head disposed on the robotic arm in FIG. 2.

The optical imaging component 112 can be provided at least partially integrated inside a housing of system 100 coupled to data bus with one or more image capture devices 122, outside of the housing as shown in FIGS. 2 and 3. The optical image component 112 and other components of the system 100 can be in communication with the data bus and the respective other components of the system 100 utilizing interface standards such as peripheral component interconnect (PCI/PCIe), universal serial bus (USB/USBII/USBIII/USB-C), Ethernet, or Firewire, to name a few. However, the present disclosure contemplates that any other interface and/or communications standards can be used.

In some scenarios, the system 100 utilizes the ultrasound component 104 with a transducer 106 to scan and image a tumor bed, to obtain structural or anatomical information about the region of interest. The system can also utilize the optical imaging component 112 with image capture device 122 to optically scan and image the same volume to obtain functional and/or metabolic information pertaining to the skin tissue or portions thereof. As used herein, the functional and/or metabolic information referenced herein can include any information pertaining to the biological function, behavior or processes at work in a particular cell or group of cells. The ultrasound and optical scanning processes will be described below in further detail. A registration process can be used to facilitate alignment of the image data acquired using the ultrasound and optical scanning methods. After the region of interest has been scanned and imaged by the system 100, the image data is processed by the system's software. The image data acquired using the ultrasound and optical scanning methods can be registered and then fused or merged to form a single image. In the fused image, the image data acquired by using ultrasound is basically superimposed over the image data acquired by using the optical scanning method described herein. The result is a hybrid image which includes detailed anatomical and/or structural data for the tumor bed with the functional data for the same tissue volume superimposed. This process can be used after tumor excision to help identify any portions of the tumor bed that may comprise cancerous tissue.

The system 100 is controlled and operated by the system control component 110, which can include a central computer with a motherboard that runs operation and control software with various parallel and connected boards that allow it to control, communicate, and monitor the various sub-components and modules of the system 100. This achieves harmonious functionality between the three main clinical components of the system 100 including the radiotherapy component 102, the robotic arm 114 and the patient motion sensing component. The system control component 110 can be communicatively connected with data repositories, including a patient data repository 118 and a system data repository 120.

The software or instructions executed by the system control component can control the system 100 functions, verify the safety mechanisms, and the service and calibration functions. The control system component 110 can be in communication with a machine-readable medium which can be static memory on which is stored one or more sets of instructions (e.g., software) embodying any one or more of the methodologies or functions described herein, including those methods illustrated herein. The instructions may also reside, completely or at least partially, within the system data repository, static memory, or within the processor, or a combination thereof, during execution thereof by the system 100. The system data repository and patient data repository and the processor also may constitute machine-readable media.

The patient data repository 118 and the system data repository 120 can be a solid-state drive, hard drive or other memory device. The patient data repository 118 can store patient-related data and treatment parameters, such as patient records, treatment session details, and disease documentation and photos. The system data repository 120 stores all system-related data and parameters, such as the system log, x-ray calibration data, and system diagnostics results. The patient data repository 118 and the system data repository 120 can be discrete devices or physically combined. One or more partitions can be used if the repositories 118 and 120 are combined, such as a single repository. Both data repositories will be mirrored and backed up to a secured and encrypted HIPAA-compliant cloud storage medium.

One example of a robotic IORT system 200 is shown in FIG. 2. The system 200 can include a base unit 201 with various components mounted thereon or connected therewith. These components can include a robotic arm 202, a radiotherapy treatment device 216, a saline reservoir 212, a saline control element 214, and a system control component 210. The base unit can also include an optical imaging component 232, an ultrasound component 234, and a data storage device 236 for storing patient and/or system data. The base unit 201 is advantageously a compact unit such as one with a 30"×30" footprint and can be mounted on casters 211 for ease of maneuverability. The base unit 201 can include a power lead for optionally providing power to all of the components housed in or connected to the base unit 201. In this regard, the base unit 201 can contain one or more computers 217 for controlling the system 200 and/or analyzing and processing data obtained from the system 200 components. A monitor 218 can also mounted to the base unit 201 for a user interface. Likewise, a terminal or an input device such as a keyboard or mouse, can be included.

A mount 203 is provided on the base unit 201 for mounting the robotic arm 202. The robotic arm 202 can include a treatment head 224 which can include removable or movable applicators for applying IORT. The robotic arm 202 is articulated with appropriate robotic joints or articulation members 204 under the control of the system control component 210. Although not shown in FIG. 2, additional articulations can also be provided at different points of robotic arm 202 to increase a number of degrees of freedom 225 of placing, orienting and moving treatment head 224. Moreover, the number of articulation points illustrated in FIG. 2 is solely for ease of illustration. The present disclosure contemplates that the any number of articulation points between mount 203 and treatment head 224 can be provided so as to provide any number of degrees of freedom in robotic arm 202 as may be required for dynamically positioning and orienting the treatment head with respect to the patient to compensate for patient body movement. A saline conduit 222 can facilitate communication of saline from the reservoir 212 and saline control component 214 to the treatment head 224. Similarly, power and/or control signals can be communicated from the radiotherapy treatment device 216 to the treatment head 224 to control and facilitate operation of the X-ray tube (not shown in FIG. 2).

The patient motion sensing and tracking described herein is advantageously implemented through the integration of physical sensing means, optical sensing means or both. The x-ray treatment head 224 can be directly mounted on or attached to the robotic arm 202. Consequently, the patient tissue movement exerted on the treatment head can be sensed through direct miniscule physical pressure that is transmitted from the treatment head to the robotic arm. These forces can be defined by associated force vectors aligned with orthogonal x, y and z coordinate axes. The force sensing can be facilitated by physical sensors 242, 244, 246, 248 located in any of several positions throughout the robotic arm. For example, in some scenarios, the physical sensors can be comprise torque sensors associated with each of a plurality of robot arm joints 204. The physical sensors can be a combination of one or more various types, such as piezo-electric, gyroscopic, solid state, and other mechanisms and materials.

To facilitate tracking of patient motion, one or more fiducial markers 226 can be optionally be placed on portions of a patient's body. In some scenarios, the fiducial markers can comprise an optical type of fiducial markers that facilitate optical tracking of position associated with the fiducial marker. The motion of the fiducial markers can be monitored by sensors 228. The sensors 228 may be disposed on a portion of the robotic arm 202 or on a sensor supporting structure 230 which provides good visibility of the patient upon whom IORT is to be performed. The sensors 228 can comprise any type of sensor suitable for monitoring patient motion. For example, in the case where the fiducial markers are of an optical type, LIDAR methods can be used to precisely detect the location of each fiducial marker. Of course, embodiments are not limited in this regard and any other suitable type fiducial marker and associated sensing system can be used. The sensor outputs are monitored by the system control component 210 and processed by one or more motion analyzing software components (tracking system software).

The tracking system software will be periodically provided with updated data from the physical sensor information received from physical sensors 242, 244, 246, 248. Concurrently, the tracking system software is also advantageously provided with fiducial marker position information generated from one or more sensor(s) 228. The tracking system software will use the received information to generate an immediate correcting x, y, z coordinate update command for the robotic arm which reflects the subtle movement of the patient tissue. The robotic arm, subsequently, shall move to the new synchronized x, y, z coordinate/location to correspond with the patient's tissue motion. This motion correction mechanism will advantageously run in a perpetual cyclical loop to constantly sense and follow the patient tissue motion generated by respiratory or other bodily functions.

Based on such analysis, the system control component 210 controls the robotic arm 202 to ensure that the treatment head 224 is moving in precise synchronization with the patient movement. For example, the treatment head can rise and fall with the respiratory action of the patient.

The treatment head 224 is shown in greater detail in FIG. 3. The treatment head can comprise an elongated tubular member 304 formed of a rigid material. The tubular member 304 is secured to an end of the robot arm by means of a base 302 comprising suitable mounting means. A balloon 306 is secured to a treatment end of the tubular member 304 by means of a collar 305 or other suitable attachment mechanism so that the balloon encloses an X-ray tube 314. Power to the X-ray tube is provided by leads 316 which pass through a sealing member 322. Ports 312a, 312b respectively facilitate attachment of fluid conduits 310a, 310b. The fluid conduit 310a allows a flow of liquid (e.g., saline) to the internal space 326 defined within the balloon. The fluid conduit 310b allows a flow of liquid (e.g., saline from the internal space 326. In an example scenario, electrical connections for operation of the X-ray tube can be provided on an end of the robotic arm adjacent to where the base 302 is attached. The leads 316 can be connected to the electrical connections on the robot arm to provide electrical power to the X-ray tube 314. Likewise, saline fluid ports (not shown) can be provided on the robotic arm. The conduits 310a, 310b can be connected to the fluid ports disposed on the robotic arm to communicate saline fluid to and from the internal space 326 of the balloon. The sealing member 322 prevents saline fluid communicated to the balloon from escaping a distal chamber 324 which may be in fluid communication with the interior space 326 of the balloon 306.

An imaging head 320 can be included on the tubular member to provide for remote operation or for documentation of treatment. A separate imaging head 330 can be disposed inside the balloon 306. Alternatively, or in addition thereto, a fiber optic member 318 can be provided within the interior of the tubular member 304. The fiber optic can extend to the internal space 326 to provide a visual image of the X-ray source during IORT setup and operations. Imaging heads 320, 330 can include components needed for supporting an imaging modality. For example, referring back to FIG. 1, a first imaging head 320 can be provided that includes image capture device 122. The second imaging head 330 can include ultrasound transducer 106. However, the present disclosure also contemplates combined functionality. That is, a single imaging head 320, 330 can incorporate ultrasound transducer 106 and image capture device 122.

In some scenarios it can be advantageous to include one or more patient motion sensors 328 disposed on the treatment head to monitor movement of a patient during IORT operations. However, the one or more sensors 328 are not required to be present on treatment head and can instead be disposed on the robotic arm or other structure to facilitate motion monitoring.

Figure 4:
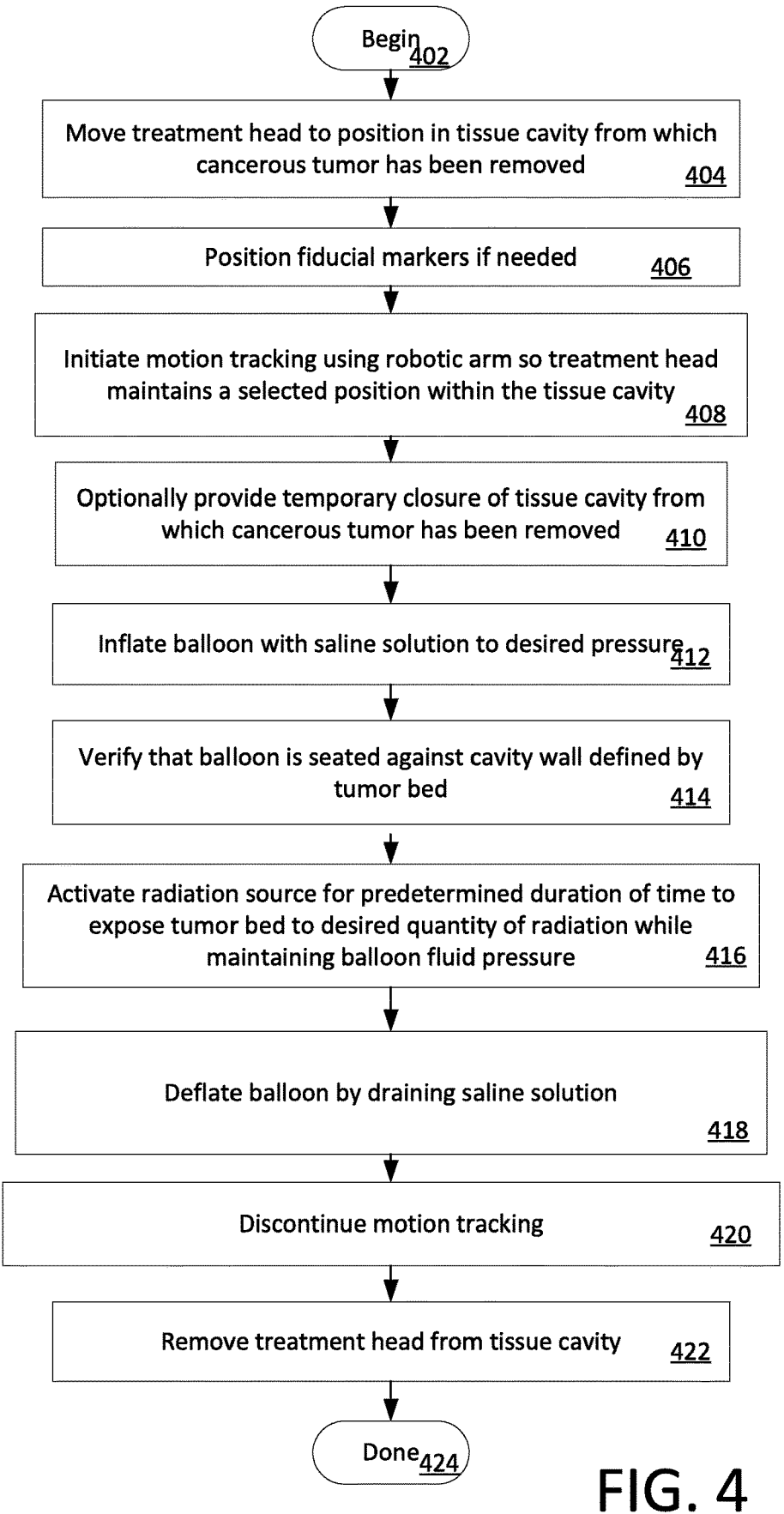
FIG. 4 is a drawing that is useful for understanding a process for robotic IORT.

Referring now to the flowchart of FIG. 4 an exemplary process for robotic IORT is described. The process begins at 402 and continues to 404 when a treatment specialist moves the treatment head so that it is positioned within a tissue cavity from which a cancerous tissue has been removed. The process then continues to step 406 where one or more fiducial markers are optionally positioned on the body of the patient. The use of fiducial markers is optional but can sometimes be helpful to facilitate motion tracking, depending on the type of sensing. At 408 the motion tracking function of the robotic arm can be initiated so the treatment head maintains a selected position within the tissue cavity. At 410, the surgeon can provide a temporary closure of the tissue cavity for purposes of facilitating robotic IORT. After the temporary closure, the IORT treatment balloon is inflated at 412 to a predetermined pressure using the saline solution. At this point, the surgeon can use one or more visualization tools to verify 414 that the walls of the balloon are uniform seated against the cavity wall defined by the tumor bed.

Once satisfied that the balloon is properly inflated and that the radiation source is in a satisfactory position, the radiation source can be activated at 416 for a predetermined period of time. Upon completion of the radiation treatment, the balloon is deflated at 418. Motion tracking can be discontinued at 420 after which the treatment head is removed from the tissue cavity at 422. The process can then ends at 424 or other treatments can be performed.

Figure 5:
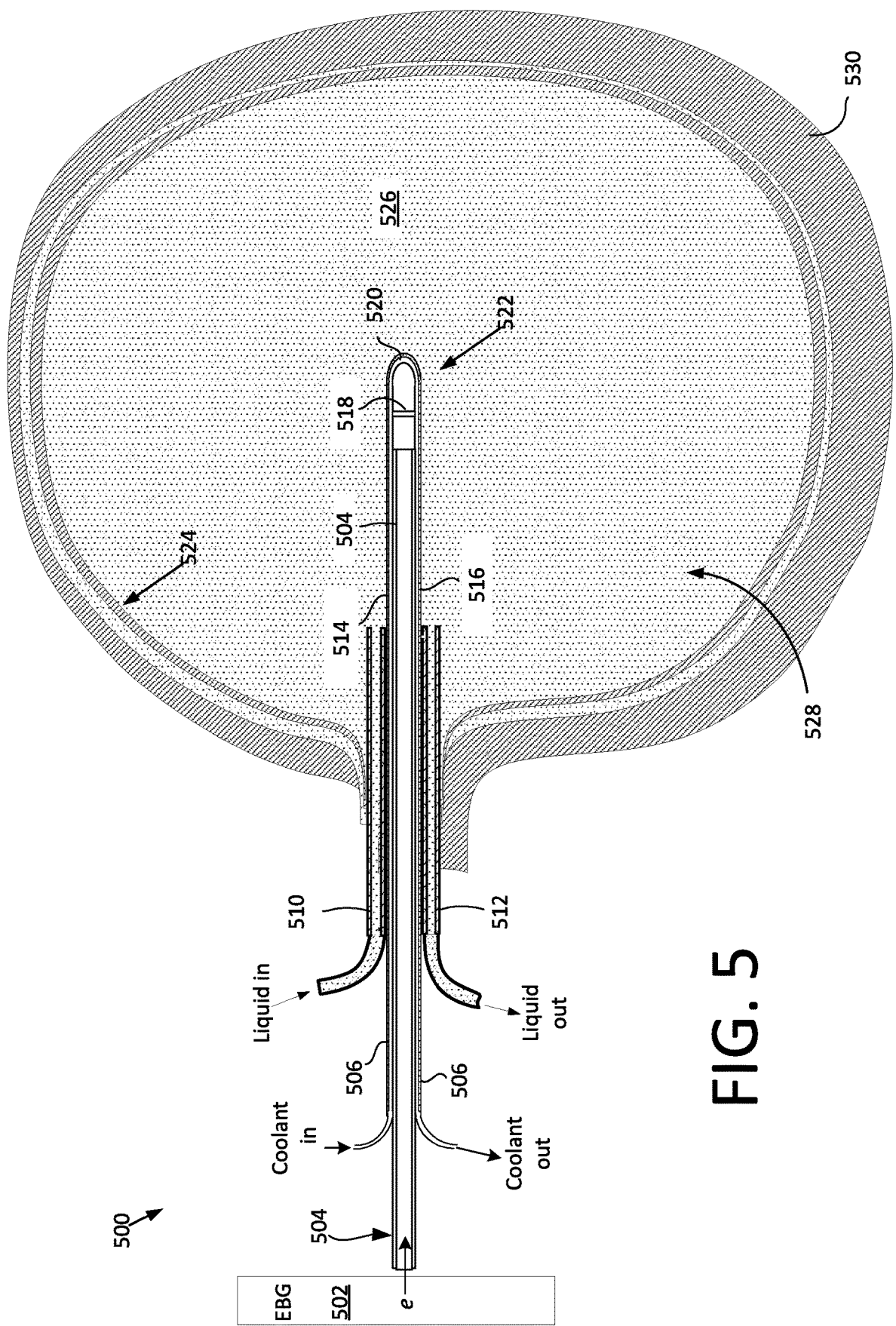
FIG. 5 is a drawing that is useful for understanding an alternative implementation of a treatment head which can be used for robotic IORT using a robotic arm.

Turning now to FIG. 5 there is shown an alternative type of IORT X-ray source 500 which can be used with the robotic IORT system described herein. Briefly, the system comprises an electron beam gun (EBG) 502 and a drift tube 504 which is supported on an end of the robotic arm 202 distal from the base. An IORT X-ray treatment head 522 resides at an end of the drift tube, distal from the EBG. The drift tube 504 is comprised of a conductive material such as stainless steel. Alternatively, the drift tube can be comprised of a ceramic material such as alumina or aluminum nitride with a conductive inner lining. The hollow inner portion of the drift tube is maintained at a vacuum pressure (e.g. a suitable vacuum pressure for purposes of embodiments described herein can be in the range below about 10−5 torr or particularly between about 10−9 torr to 10−7 torr).

Electrons e comprising an electron beam are accelerated by the EBG toward an X-ray target 518. These electrons will have significant momentum when they arrive at the entry aperture of the drift tube. The hollow interior of the drift tube is maintained at a vacuum pressure and at least the inner lining of the tube is maintained at ground potential. Accordingly, the momentum imparted to the electrons by EBG 502 will continue to ballistically carry the electrons down the length of the drift tube at very high velocity (e.g. a velocity approaching the speed of light) toward the X-ray target 518. It will be appreciated that as the electrons are traveling along the length of the drift tube 504, they are no longer electrostatically accelerated.

The X-ray target 518 is comprised of a disk-shaped element which is disposed transverse to the direction of electron beam travel. For example, the disk-shaped element can be disposed in a plane which is approximately orthogonal to the direction of electron beam travel. In some embodiments, the X-ray target can enclose an end portion of the drift tube distal from the electron gun to facilitate maintenance of the vacuum pressure within the drift tube. The X-ray target 518 can be almost any material, however it is advantageously comprised of a material such as molybdenum, gold, or tungsten which has a high atomic number so as to facilitate the production of X-rays at relatively high efficiency when bombarded with electrons.

In other respects the arrangement shown in FIG. 5 is similar to that described herein with respect to FIG. 3. An interstitial space between the X-ray source (i.e., treatment head 522) and a wound cavity can be filled with saline fluid 526 disposed within a fluid bladder 524. The fluid bladder can be an elastic balloon-like member which is inflated with a fluid 526, such as saline, so as to fill an interstitial space 528 between the X-ray source and a tissue wall 530 (e.g. a tissue wall comprising a tumor bed). Fluid conduits 510, 512 disposed in or on the robotic arm 202 can facilitate a flow of fluid to and from the interior of the fluid bladder. Such an arrangement can help enhance the uniformity of irradiation of the tumor bed by positioning the entire tissue wall a uniform distance away from the X-ray source to facilitate a more consistent radiation exposure. The generation of X-rays at X-ray target 518 can generate substantial amounts of heat. So in addition to the fluid 526 which fills the interstitial space, a separate flow of coolant can be provided to the treatment head through coolant conduits 506.

The various components comprising the X-ray source 500 (e.g., EBG 502, the drift tube 504, and treatment head 522) can be mounted on the robotic arm. The position of the X-ray source can be controlled as described with respect to FIGS. 1-4 so that movement of the X-ray source is coordinated with natural body motion of the patient undergoing treatment. Of course, the methods for robotic IORT are not limited to the particular IORT X-ray radiation sources described above. Instead, any suitable X-ray source now known or known in the future can be used to facilitate the robotic IORT methods and systems described herein.

Figure 6:
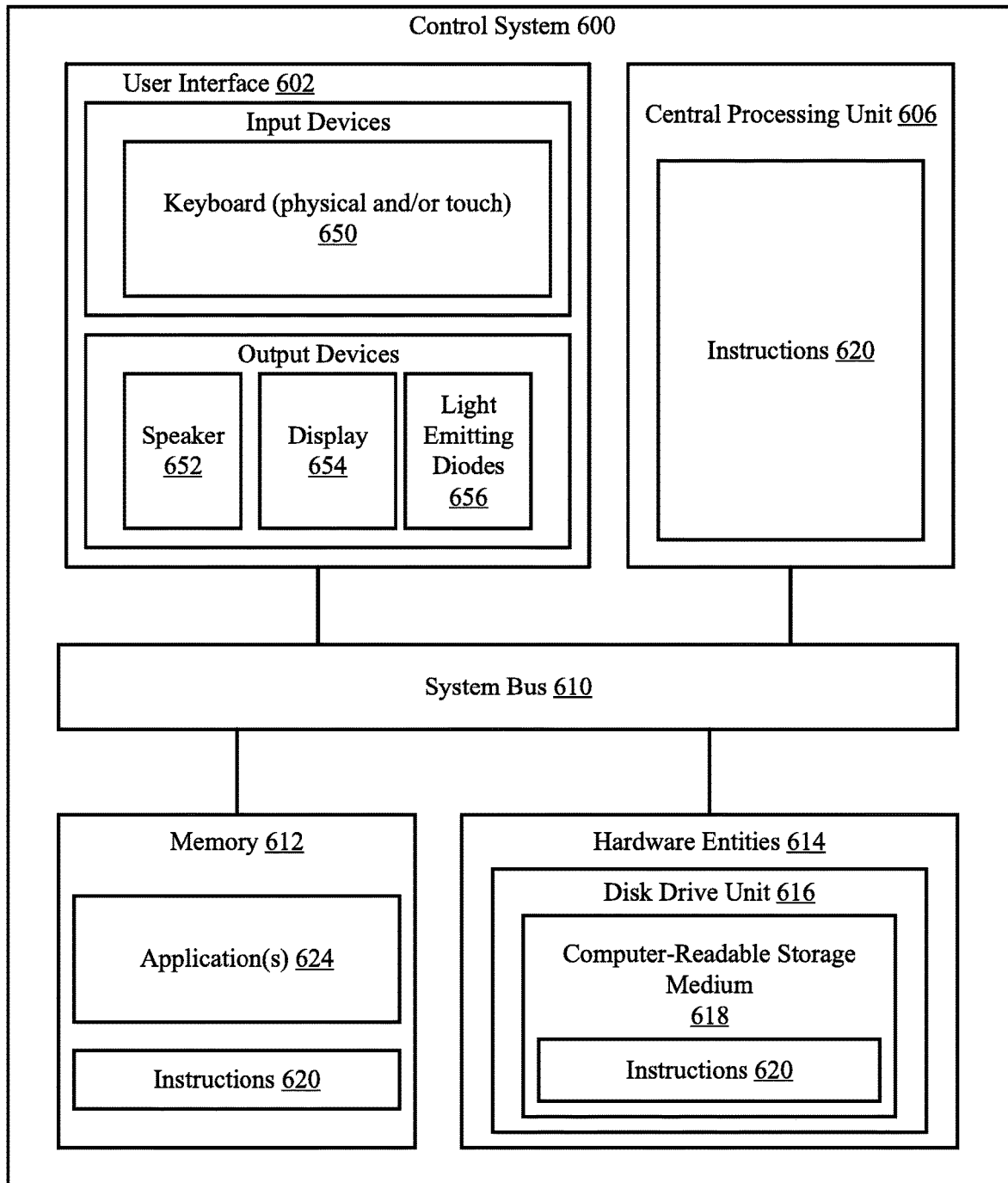
FIG. 6 is a block diagram that is useful for understanding a control system which can be used for facilitating robotic IORT as described herein.

Referring now to FIG. 6, there is provided an illustration of an exemplary control system 600 which can be used for controlling a robotic IORT system as described herein. The control system can include, but is not limited to, machines (or computing devices) running a Windows OS (e.g., a personal computer or server). Such machines (or computing devices) are well known in the art, and will not be described in detail herein. Still, it should be understood that such machines are modified to implement all or a portion of the methods described herein. Such modifications can include software modifications, hardware modification or a combination of both.

Control system 600 may include more or less components than those shown in FIG. 6. However, the components shown are sufficient to disclose an illustrative embodiment implementing the present solution. The hardware architecture of FIG. 6 represents one embodiment of a representative control system or computing device configured to facilitate the IORT tracking control operations described herein.

Some or all the components of the control system 600 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 6, the control system 600 comprises a user interface 602, a Central Processing Unit ("CPU") 606, a system bus 610, a memory 612 connected to and accessible by other portions of computing device 600 through system bus 610, and hardware entities 614 connected to system bus 610. The user interface can include input devices and output devices, which facilitate user-software interactions for controlling operations of the computing device 600. The input devices include, but are not limited, a physical and/or touch keyboard 650. The input devices can be connected to the computing device 600 via a wired or wireless connection (e.g., a Bluetooth® connection). The output devices include, but are not limited to, a speaker 652, a display 654, and/or light emitting diodes 656.

At least some of the hardware entities 614 perform actions involving access to and use of memory 612, which can be a Random Access Memory ("RAM"), a disk drive and/or a Compact Disc Read Only Memory ("CD-ROM"). Hardware entities 614 can include a disk drive unit 616 comprising a computer-readable storage medium 618 on which is stored one or more sets of instructions 620 (e.g., software code) configured to implement one or more of the methodologies, procedures, or functions described herein. The instructions 620 can also reside, completely or at least partially, within the memory 612 and/or within the CPU 606 during execution thereof by the computing device 600. The memory 612 and the CPU 606 also can constitute machine-readable media. The term "machine-readable media", as used here, refers to a single medium or multiple media (e.g., a centralized or distributed database, and/or associated caches and servers) that store the one or more sets of instructions 620. The term "machine-readable media", as used here, also refers to any medium that is capable of storing, encoding or carrying a set of instructions 620 for execution by the control system 600 and that cause the control system 600 to perform any one or more of the methodologies of the present disclosure.

In some scenarios, the hardware entities 614 include an electronic circuit (e.g., a processor) programmed for facilitating control over the robotic arm. In this regard, it should be understood that the electronic circuit can access and run application(s) 624 installed on the computing device 600.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

I claim:

1. A robotic system for intraoperative radiation therapy, comprising:
a robotic arm comprised of a plurality of movable joints and secured at a first end to a base;
a treatment head disposed on a second end of the robotic arm distal from the base;
the treatment head comprising at least one X-ray component configured to facilitate generation of therapeutic radiation in the X-ray wavelength range;+
a plurality of torque sensors respectively associated with the plurality of movable joints and configured to sense forces exerted on the plurality of movable joints through the treatment head as a result of movement of a patient body; and
a control system comprised of an electronic circuit, the control system responsive to patient motion data from the plurality of torque sensors and configured to facilitate dynamic position control of the treatment head by selectively varying a position of at least one of the movable joints comprising the robotic arm responsive to the patient motion data;
wherein the dynamic position control is configured to minimize a relative motion as between the treatment head and all surfaces of a tumor bed defining a cavity internal of the patient while using the treatment head to perform a radiation treatment, whereby variations in distance as between the treatment head and all surfaces of the tumor bed are minimized during a respiratory action of the patient body.

2. The robotic system according to claim 1, wherein the control system is configured to selectively control the motion of the treatment head in three orthogonal directions.

3. The robotic system according to claim 1, wherein the control system is further configured to selectively control a rotation of the treatment head within the cavity to minimize angular variations of the source of the therapeutic radiation relative to locations comprising the surfaces of the tumor bed under conditions involving the movement of the patient body.

4. The robotic system according to claim 1, further comprising an optical sensor configured to detect a position of at least one fiducial marker.

5. The robotic system according to claim 1, wherein the robotic arm supports a plurality of utility channels to facilitate radiation treatment functions and operations, said utility channels selected from the group of fluid utility channels, electrical utility channels, and data utility channels.

6. The robotic system according to claim 5, further comprising an inflatable balloon member disposed to enclose at least a distal end of the treatment head from which the therapeutic radiation originates, wherein the fluid utility channels are configured to communicate a fluid to and from an interior of the inflatable balloon member.

7. The robotic system according to claim 5, further comprising at least one imaging device supported by the robotic arm or the treatment head to facilitate optical guidance of the treatment head within a cavity left by a cancerous tumor after excision thereof, and wherein data carried by the data utility channel comprises video data.

8. The robotic system according to claim 5, further comprising an ultrasound probe supported on the treatment head to facilitate ultrasound imaging of a tumor bed within the patient remaining after excision of a cancerous tumor, wherein data carried by the data utility channel comprises ultrasound imaging data.

9. A method for intraoperative radiation therapy, comprising:
securing a treatment head on a mounting end of the robotic arm distal from a robotic arm base;
including as part of the treatment head at least one X-ray component configured to facilitate generation of therapeutic radiation in the X-ray wavelength range;
detecting movement of a patient body by coupling forces exerted on the treatment head as a result of the movement to a plurality of torque sensors which are respectively associated with a plurality of movable joints of the robotic arm; and
responsive to patient motion data received from the plurality of torque sensors, dynamically controlling a position of the treatment head with a control system comprising an electronic processor by causing a position variation in at least one of the movable joints comprising the robotic arm, whereby variations in distance as between the treatment head and all surfaces of a cavity defined by the tumor bed are minimized during a respiratory action of the patient body.

10. The method according to claim 9, wherein the control system selectively controls the motion of the treatment head in three orthogonal directions.

11. The method according to claim 9, wherein the control system selectively controls a rotation of the treatment head within the cavity to minimize angular variations of the source of the therapeutic radiation relative to locations comprising the surfaces of the tumor bed under conditions involving the movement of the patient body.

12. The method according to claim 9, further comprising using at least one optical sensor to optically detect a position of at least one fiducial marker.

13. The method according to claim 9, further comprising supporting with the robotic arm a plurality of utility channels to facilitate radiation treatment functions and operations, said utility channels selected from the group of fluid utility channels, electrical utility channels, and data utility channels.

14. The method according to claim 13, further comprising disposing an inflatable balloon member to enclose at least a distal end of the treatment head from which the therapeutic radiation originates, and communicating with the fluid utility channels a fluid to and from an interior of the inflatable balloon member.

* * * * *